United States Patent
Gilmour

[11] Patent Number: 5,984,766
[45] Date of Patent: Nov. 16, 1999

[54] SAMPLE REMOVING TOOL

[75] Inventor: Kenneth S. Gilmour, Nottinghamshire, United Kingdom

[73] Assignee: Rolls-Royce and Associates, Limited, Derby, United Kingdom

[21] Appl. No.: 08/751,698

[22] Filed: Nov. 18, 1996

[30] Foreign Application Priority Data

Nov. 21, 1995 [GB] United Kingdom ................... 9523808

[51] Int. Cl.⁶ ............................ B26D 1/18; G01N 1/04
[52] U.S. Cl. ..................... 451/211; 083/327; 083/329; 083/647.5; 083/861
[58] Field of Search ........................... 83/327, 329, 330, 83/471.1, 647.5, 337, 472, 473, 490, 491, 671, 861, 917; 451/211, 271

[56] References Cited

U.S. PATENT DOCUMENTS

| Re. 30,598 | 5/1981 | Spencer | 83/329 X |
| 4,041,813 | 8/1977 | Spencer | 83/327 X |
| 4,424,649 | 1/1984 | Vincent et al. | 451/213 |
| 4,843,932 | 7/1989 | Weber et al. | 83/647.5 X |
| 4,845,896 | 7/1989 | Mercaldi | 451/121 |
| 4,856,233 | 8/1989 | Mercaldi | 451/28 |
| 4,914,997 | 4/1990 | Belvederi | 83/595 X |
| 5,152,203 | 10/1992 | Wierschke | 83/329 X |
| 5,289,747 | 3/1994 | Wunderlich | 83/329 X |
| 5,557,997 | 9/1996 | Wunderlich et al. | 83/329 X |

FOREIGN PATENT DOCUMENTS

| 253666 | 4/1967 | Australia | 83/329 |
| 692702 | 10/1979 | U.S.S.R. | 83/647.5 |
| 2 282 778 | 4/1995 | United Kingdom . | |

Primary Examiner—Clark F. Dexter
Attorney, Agent, or Firm—W. Warren Taltavull; Farkas & Manelli PLLC

[57] ABSTRACT

A sample removing tool comprises two partly spherical blades which are rotatably mounted on a carrier member about parallel axes. The cutting edges of the blades face each other and a portion of the cutting edges are arranged to lie in a nominal circle. The carrier member is rotatably mounted on a support member about an axis, the axis is perpendicular to a plane containing the nominal circle and passes through the center of the nominal circle. The axes of the blades are inclined to the axis of rotation of the carrier member. The blades are rotated about their axes and the carrier member is rotated about its axis such that the cutting edges of the blades move along the circumference of the nominal circle to cut a sample from a surface of a component arranged perpendicular to and intersecting the nominal circle.

15 Claims, 2 Drawing Sheets

SAMPLE REMOVING TOOL

FIELD OF THE INVENTION

The present invention relates to machine tools for removing samples from the surfaces of components with minimum damage to the surface of the component being sampled.

BACKGROUND OF THE INVENTION

It is known from published International Patent application WO8806722A, to use a half spherical blade which rotates about an axis to provide a cutting action and the half spherical blade is articulated about an axis such that the blade follows an arcuate path to cut and separate a sample from the surface of a component.

It is also known from our prior UK Patent application GB2282778A to use a part spherical blade which reciprocates about an axis to provide a cutting action and the part spherical blade is moved through an arcuate path to cut a sample from the surface of a component.

SUMMARY OF THE INVENTION

The present invention seeks to provide a novel machine tool for removing a sample from a component.

Accordingly the present invention provides a sample removing tool comprising a first blade having a circular cutting edge, a second blade having a circular cutting edge, carrier means for carrying the first and second blades, the first and second blades being rotatably mounted on the carrier means about first and second axes of rotation respectively, a portion of the cutting edge of the first and second blades is arranged to lie on the circumference of a nominal circle, drive means to rotate the first and second blades about the first and second axes respectively, support means for supporting the carrier means, the carrier means being rotatably mounted on the support means to rotate about a third axis, second drive means to rotate the carrier means about the third axis, the third axis is perpendicular to a plane containing the nominal circle and passes through the centre of the nominal circle, the first and second axes of the first and second blades respectively are inclined to the third axis such that as the carrier means rotates around the third axis a portion of the cutting edges of the first and second blades lies on the circumference of the nominal circle.

Preferably the first and second blades are rotatably mounted on the carrier means 180° apart relative to the axis of the nominal circle, the first and second axes are parallel.

Preferably the drive means comprises a single power unit arranged to drive the first and second blades.

Preferably the single power unit is mounted on the carrier means.

The single power unit may be an electric motor, a hydraulic motor, a pneumatic motor or an internal combustion engine, preferably a wankel engine.

Preferably the single power unit is arranged to drive a shaft having an axis parallel to the first and second axes, means to transmit drive from the shaft to the first and second blades.

The means to transmit drive may comprise pulleys on the first and second blades, pulleys on the drive shaft and belts transmitting drive from the pulleys on the drive shaft to the pulleys on the first and second blades. The belts may be toothed belts, flat belts or V-shaped belts.

The means to transmit drive may comprise gears on the first and second blades, and gears on the drive shaft which engage the gears on the first and second blades to transmit drive from the drive shaft to the first and second blades.

The means to transmit drive may comprise wheels on the drive shaft frictionally engaging the first and second blades.

Alternatively the drive means may comprise two power units arranged to drive the first and second blades.

Preferably each of the power units is mounted on a respective one of the first and second blades.

The power units may be electric motors, hydraulic motors, pneumatic motors or internal combustion engines, preferably a wankel engine.

Preferably the second drive means comprises a pneumatic rotary actuator, a hydraulic rotary actuator, an electric rotary actuator, preferably an electric motor.

Preferably the first and second blades have a part spherical shape.

The sample removing tool may be positioned in a housing.

The support means may be secured to an arm of a robotic manipulator.

BRIEF DESCRIPTION OF THE DRAWINGS

The present invention will be more fully described by way of example, in which.

DETAILED DESCRIPTION OF THE INVENTION

Figure 1:
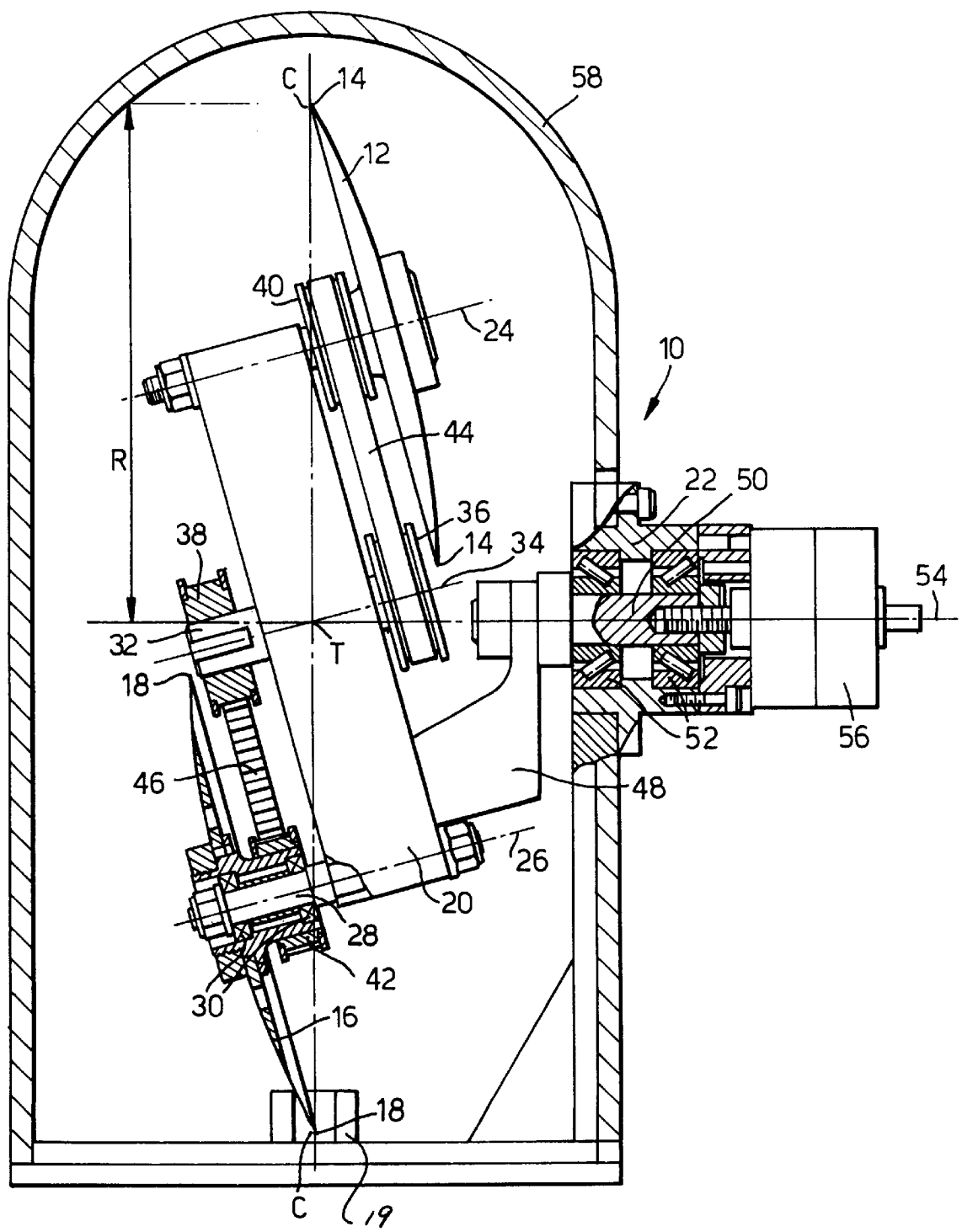
FIG. 1 is a longitudinal cross-sectional view through a sample removing tool according to the present invention.

A sample removing tool 10, shown in FIG. 1, comprises a first blade 12, a second blade 16, a carrier member 20 and a support member 22.

The first blade 12 has a part spherical shape and has a circular cutting edge 14. Similarly the second blade 16 has a part spherical shape and has a circular cutting edge 18. The first blade 12 and the second blade 16 are rotatably mounted on the carrier member 20 about first and second axes of rotation 24 and 26 respectively. The first and second blades 12 and 16 are rotatably mounted on spindles 28 carried by the carrier member 20 by a pair of ball bearings 30. The axes of rotation 24 and 26 of the first and second blades 12 and 16 respectively are parallel to each other. A portion of the cutting edges 14 and 18 of the first and second blades 12 and 16 are arranged to lie on a nominal circle C which has a diameter R and a centre T. The first and second blades 12 and 16 are arranged so that their cutting edges 14 and 16 face each other.

The carrier member 20 contains an electric motor 35 which is arranged to drive a drive shaft 32 which is rotatably mounted on the carrier member 20. The axis 34 of the drive shaft 32 is arranged to be parallel to the axes 24 and 26 of rotation of the first and second blades 12 and 16 respectively. The axes 24, 26 and 34 of the first and second blades 12 and 16 respectively and the drive shaft 32, in this example, are arranged in a common plane. The drive shaft 32 has first and second pulleys 36 and 38 arranged at its opposite ends, the first blade 12 has a pulley 40 and the second blade 16 has a pulley 42. A first drive belt 44 is provided which engages the first pulley 36 on the drive shaft 32 and the pulley 40 on the first blade 12 to transmit drive from the electric motor to the first blade 12. Similarly a second drive belt 46 is provided which engages the second pulley 38 on the drive shaft 32 and the pulley 42 on the second blade 16 to transmit drive from the electric motor to the second blade 16. The first and second drive belts 44 and 46, in this example, are provided with teeth which engage teeth on the pulley. However it would be equally possible to use flat belts or V-shaped belts, or even to use two chains.

The carrier member 20 has an arm 48 which is rotatably mounted on the support member 22. A spindle 50, secured to the arm 48, is rotatably mounted on the support member 22 by two opposed tapered roller bearings 52. The axis 54 of the spindle 50 is perpendicular to a plane containing the nominal circle C and the axis 54 passes through the centre T of the nominal circle.

The axes 24 and 26 of the first and second blades 12 and 16 respectively are inclined at a common angle to the axis 54 of the spindle 50.

The support member 22 has at least one pneumatic rotary motor in actuator 56 which is arranged to drive the spindle 50 so as to rotate the carrier member 20 around the axis 54.

The whole of the sample removing tool 10 is enclosed in a housing 58 which includes a support platform 21 for the component 19.

Thus it can be seen that the first and second blades 12 and 16 are arranged 180° apart relative to the centre T of the circle C.

In operation to cut a sample from a component 19, the component is arranged such that the surface of the component intersects normally with the nominal circle C. The first and second blades 12 and 16 are rotated about their axes of rotation 24 and 26, and the carrier member 20 is rotated about the axis 54. This causes the cutting edges 14 and 18 of the first and second blades 12 and 16 respectively to move along the circumference of the nominal circle C. In moving along the circumference of the nominal circle the first blade 12 makes one cut in the surface of the component 19 and the second blade 16 makes another cut in the surface of the component, the two cuts together defining a boat shaped (i.e., generally V-shaped) sample with the original surface of the component.

The shape of the sample of component 19 is dictated by the diameter of the nominal circle, the diameter of the first and second blades, this determines the angle between the axis of rotation of the carrier and the axes of rotation of the first and second blades.

The cutting edges 14 and 18 of the first and second blades 12 and 16 are preferably coated with an abrasive medium to enable cutting of hard materials.

Although the description has referred to the use of an electric motor as the power unit for driving the first and second blades it may be equally practical to use a hydraulic motor, a pneumatic motor, or an internal combustion engine, preferably a wankel engine.

Figure 2:
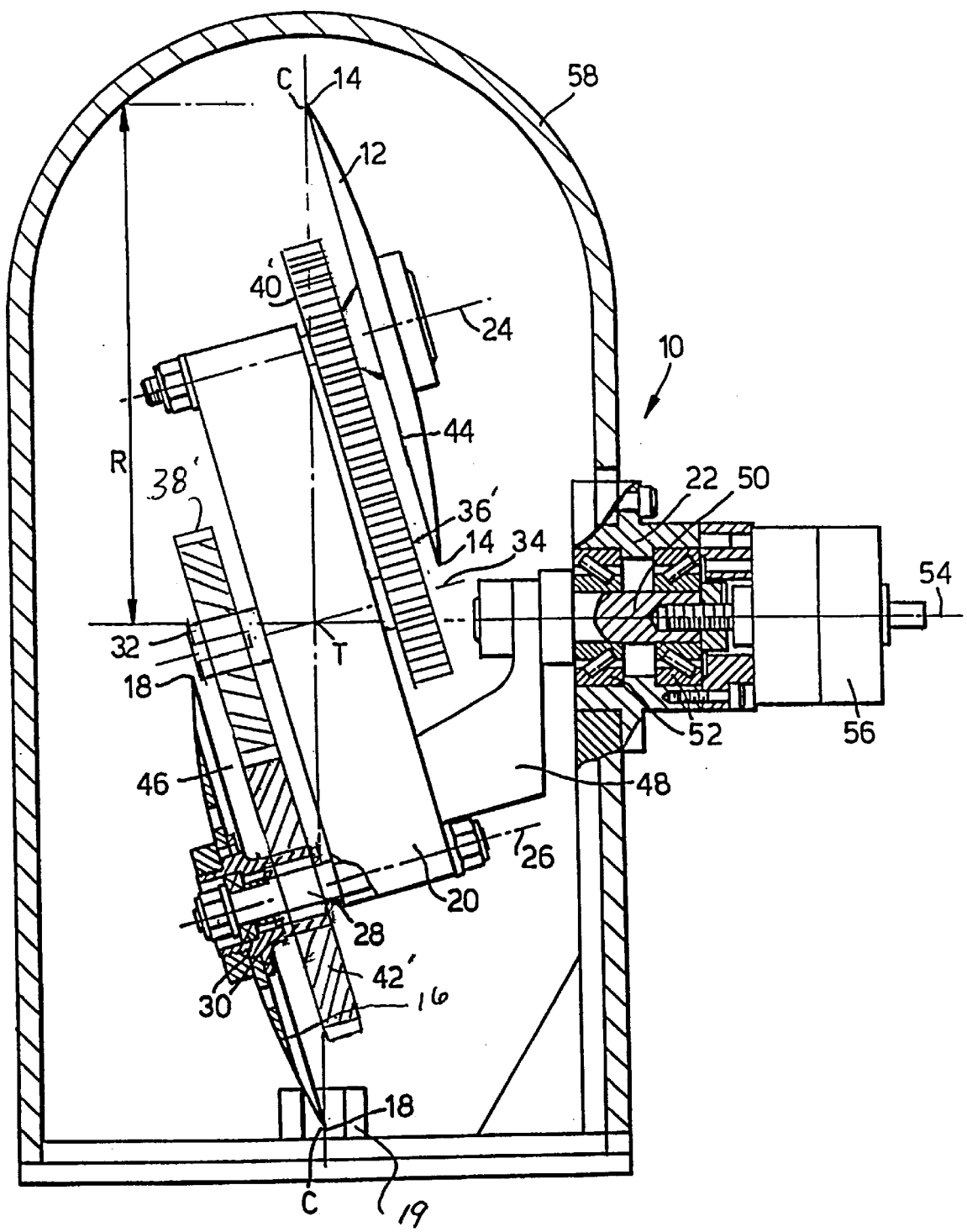
FIG. 2 illustrates schematically another form of the invention.

Although the description has referred to the use of pulleys and belts to transmit drive to the first and second blades, it is equally possible as shown in FIG. 2 to provide gears 40' and 42' on the first and second blades, and gears 36' and 38' on the drive shaft which engage the gears on the first and second blades. Alternatively the means to transmit drive may comprises wheels on the drive shaft frictionally engaging the first and second blades.

A further possibility is to provide two power units arranged to drive the first and second blades. In this arrangement each of the power units is mounted on a respective one of the first and second blades. Each power units may drive its respective blade directly or indirectly via drive belts, gears etc.

A further possibility is to provide a remote power unit and transmit drive to the first and second blades by a flexible drive shaft.

Although the description has referred to the use of a pneumatic rotary motor to drive the carrier member it is equally practicable to use a hydraulic rotary actuator, an electric rotary actuator or an electric motor.

The invention is not limited to an arrangement where the first and second blades are arranged on parallel axes of rotation, however this is the preferred arrangement. It may be possible to arrange for the first and second blades to be rotatably mounted on the carrier member in any arrangement such that as the carrier member is rotated about its axis of rotation, perpendicular to the nominal circle and passing through the centre of the nominal circle, and the axes of rotation of the blades are inclined to the axis of rotation of the carrier, a portion of the cutting edges of the first and second blades lies on the circumference of the nominal circle.

Although the invention has described the use of part spherical blades it may be possible to use circular blades which have circular cutting edges.

The sample removing tool of the present invention has a number of advantages compared to the prior art. The sample removing tool has a simple mechanical arrangement, it is relatively lightweight and small in size. There is low reaction force when cutting. The mechanical principal is scalable in size. The controls required for the tool are very simple. These advantages make the sample removing tool highly suitable for use in hazardous environments, in these circumstances the sample removing tool is mounted on the arm of a robotic manipulator.

The sample removing tool produces a boat shaped sample. A boat shaped sample has the advantage in that it is particularly suitable for collection of samples containing linear features, defects such as cracks, for examination or testing. In many cases it is the extremities of the defects which are of most interest, and the boat shaped sample removed by the sample removing tool of the present invention enables these defects to be removed from the component with the minimum loss of material from the component. Additionally the boat shaped indentation left in the component is easy to fill with weld material after the sample has been removed. The sample removing tool of the present invention does not leave re-entrant kerf slots in the component, unlike the sample removing tool described in GB2282778A.

I claim:

1. A sample removing tool for removing a sample from a surface of a component, said tool comprising a first blade having a circular cutting edge, a second blade having a circular cutting edge, carrier means for carrying the first and second blades, and support means for supporting the carrier means, the first and second blades being rotatably mounted on the carrier means about first and second axes of rotation respectively, a portion of the cutting edge of the first and second blades being arranged to lie on the circumference of a nominal circle, first drive means to rotate the first and second blades about the first and second axes respectively, the carrier means being rotatably mounted on the support means to rotate about a third axis, second drive means to rotate the carrier means about the third axis, the third axis being perpendicular to a plane containing the nominal circle and passing through the center of the nominal circle, the carrier means having a first side at one axial end of the carrier means and a second side at the other axial end of the carrier means, the first blade being mounted on a first spindle defining the first axis of rotation and extending from the first side of the carrier means and the second blade being mounted on a second spindle defining the second axis of rotation and extending from the second side of the carrier means such that the first and second blades are on opposite sides of the carrier means, the carrier means being inclined such that the first and second spindles are each inclined to said third axis of rotation, said carrier means having a center of rotation and the center of the nominal circle coinciding with the center of rotation of the carrier means, whereby the first and second axes of rotation of the first and second blades respectively are inclined to the third axis such that with the surface of the component being disposed to extend in a plane lying substantially perpendicular to said nominal circle as the carrier means rotates around the third axis, a portion of the cutting edges of each of the first and second blades lies on the circumference of the nominal circle and the cutting edge of the first blade makes a first cut in the surface of the component at an angle to the surface of the component, and the cutting edge of the second blade makes a second cut in the surface of the component at an angle to the surface of the component, the second cut intersecting the first cut to define a substantially V-shaped sample.

2. A sample removing tool as claimed in claim 1 in which the first and second blades are rotatably mounted on the carrier means 180° apart relative to the axis of the nominal circle, and wherein the first and second axes are parallel.

3. A sample removing tool as claimed in claim 2 in which the first drive means comprises a single power unit operably connected to the first and second blades to drive the first and second blades.

4. A sample removing tool as claimed in claim 3 in which the single power unit is mounted on the carrier means.

5. A sample removing tool as claimed in claim 3 or claim 4 in which the single power unit is selected from the group comprising an electric motor, a hydraulic motor, a pneumatic motor and an internal combustion engine.

6. A sample removing tool as claimed in claim 3 in which the first drive further comprises a shaft, and the single power unit drives the shaft, the shaft having an axis parallel to the first and second axes, and wherein the first drive further comprises means to transmit drive from the shaft to the first and second blades.

7. A sample removing tool as claimed in claim 6 in which the means to transmit drive comprises pulleys on the first and second blades, pulleys on the drive shaft and belts transmitting drive from the pulleys on the drive shaft to the pulleys on the first and second blades.

8. A sample removing tool as claimed in claim 7 in which the belts are selected from the group comprising toothed belts, flat belts and V-shaped belts.

9. A sample removing tool as claimed in claim 6 in which the means to transmit drive comprises gears on the first and second blades, and gears on the drive shaft which engage the gears on the first and second blades to transmit drive from the drive shaft to the first and second blades.

10. A sample removing tool as claimed in claim 1 in which the second drive means is selected from the group comprising a pneumatic rotary actuator, a hydraulic rotary actuator, an electric rotary actuator and an electric motor.

11. A sample removing tool as claimed in claim 1 in which the first and second blades have a part spherical shape.

12. The sample removing tool claimed in claim 1 wherein a housing encloses at least the carrier means and the first and second blades.

13. A sample removing tool as claimed in claim 1 further including a housing having a support platform extending perpendicular to the nominal circle and on which the component is placed, and wherein the third axis of rotation is parallel to the support platform.

14. A sample removing tool as claimed in claim 1 further including a housing having a support platform extending perpendicular to the nominal circle and on which the component is placed and wherein the axes of rotation of the first and second blades are inclined to the support platform and the blades are inclined to the support platform.

15. A sample removing tool for removing a sample from a surface of a component, said tool comprising a first blade having a circular cutting edge, a second blade having a circular cutting edge, carrier means for carrying the first and second blades, and support means for supporting the carrier means, the first and second blades being rotatably mounted on the carrier means about first and second axes of rotation respectively, a portion of the cutting edge of the first and second blades being arranged to lie on the circumference of a nominal circle, drive means to rotate the first and second blades about the first and second axes respectively, the carrier means being rotatably mounted on said support means to rotate about a third axis of rotation, second drive means to rotate the carrier means about the third axis, the third axis being perpendicular to a plane containing the nominal circle and passing through the center of the nominal circle, the carrier means having a first side at one axial end of the carrier means and a second side at the other axial end of the carrier means, the carrier means having a first end at one radial end of the carrier means and a second end at the other diametrically opposite radial end of the carrier means relative to the axis of the nominal circle, the first and second blades being rotatably mounted on the carrier means at the first and second diametrically opposite radial ends respectively of the carrier means relative to the axis of the nominal circle, the first and second axes of rotation being parallel to each other, the first blade being mounted on a first spindle defining the first axis of rotation and extending from the first side of the carrier means and the second blade being mounted on a second spindle defining the second axis of rotation and extending from the second side of the carrier means such that the first and second blades are on opposite sides of the carrier means, the carrier means being inclined such that the first and second spindles are each inclined to said third axis of rotation, said carrier means having a center of rotation and the center of the nominal circle coinciding with the center of rotation of the carrier means, whereby the first and second axes of rotation of the first and second blades respectively are inclined to the third axis such that, with the surface of the component being disposed to extend generally in a plane lying substantially perpendicular to said nominal circle as the carrier means rotates around the third axis, a portion of the cutting edges of each of the first and second blades lies on the circumference of the nominal circle and the cutting edge of the first blade makes a first cut in the surface of the component at an angle to the surface of the component and the cutting edge of the second blade makes a second cut in the surface of the component at an angle to the surface of the component, the second cut intersecting the first cut to define a generally V-shaped sample.

* * * * *